US000001809H

United States Statutory Invention Registration [19]

[11] Reg. Number: H1,809

Adams et al.

[45] Published: Oct. 5, 1999

[54] PROCESS FOR MAKING OXIMES AND USE THEREOF TO PREPARE CYCLIC UREA FUNGICIDES

[75] Inventors: Charles De Witt Adams, Newark; George Chihshu Chiang, Wilmington; Simon Lingqi Xu, Newark, all of Del.

[73] Assignee: E. I. du Pont de Nemours and Company, Wilmington, Del.

[21] Appl. No.: 09/056,689

[22] Filed: Apr. 8, 1998

Related U.S. Application Data

[60] Provisional application No. 60/043,880, Apr. 10, 1997.

[51] Int. Cl.[6] ..... C07D 249/08

[52] U.S. Cl. ..... 548/262.2

*Primary Examiner*—Charles T. Jordan
*Assistant Examiner*—Meena Chelliah

[57] ABSTRACT

An advantageous process for preparing agriculturally suitable precursor compositions containing a compound of Formula IV is disclosed. The process involves (a) reacting a compound of Formula V with a nitrosating agent to provide a diazonium ion of Formula Va, (b) reacting the diazonium ion with a compound of Formula VI in the presence of a copper salt catalyst to obtain a reaction product containing the compound of Formula IV and greater than 100 ppm copper (based on the weight of Formula IV compound), and (c) separating copper from the Formula IV compound to obtain a purified product composition containing the compound of Formula IV and less than 10 ppm copper (based on the weight of Formula IV compound).

IV

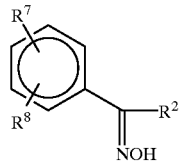

V

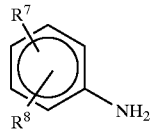

Va

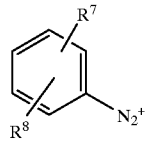

VI

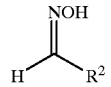

A method for preparing a cyclic urea fungicides of Formula I is disclosed, which involves (1) preparing an agriculturally suitable precursor composition as indicated (2) reacting the oxime of Formula IV from said precursor composition with a compound of Formula III to provide a compound of Formula II, and (3) reacting the compound of Formula II with a compound of Formula $MOR^1$.

I

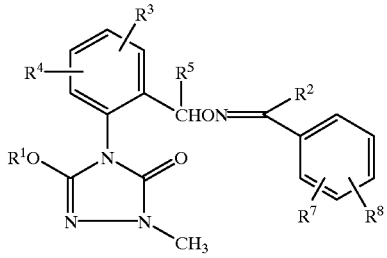

II

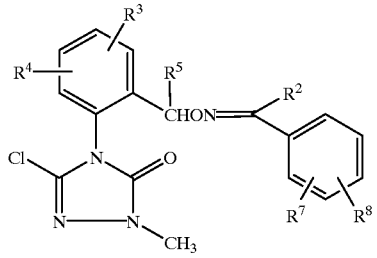

III

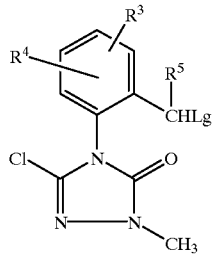

Suitable $R^1$–$R^5$, $R^7$, $R^8$ and Lg are indicated in the specification.

2 Claims, No Drawings

---

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR MAKING OXIMES AND USE THEREOF TO PREPARE CYCLIC UREA FUNGICIDES

This application claims the priority benefit of U.S. Provisional application Ser. No. 60/043,880, filed Apr. 10, 1997.

FIELD OF THE INVENTION

This invention pertains to processes which are useful for preparing oximes and use thereof to prepare cyclic urea fungicides.

BACKGROUND OF THE INVENTION

Oximes are important intermediates in agricultural and pharmaceutical industry. For example, PCT International Publication No. WO 95/14009 discloses oximes useful for the preparation of cyclic urea fungicides for crop protection. Conventional preparation of oximes from ketone precursors is restricted by the high cost of the ketones. See March, J. Advanced Organic Chemistry; 3$^{rd}$ Ed., John Wiley: New York, 1985, p 1166.

*J Chem. Soc.,* 1954, 1297 discusses the preparation of aromatic aldehydes and ketones from diazonium salts. The use of copper salt catalysts is disclosed; as is the formation of certain oxime intermediates. It is desirable to minimize the presence of heavy metals such as copper from agricultural compositions and their precursors to enhance their suitability for broad spectrum application. Nevertheless, there is a continuing need to develop processes useful for efficiently preparing cyclic urea fungicides.

SUMMARY OF THE INVENTION

This invention involves an advantageous process for preparing an agriculturally suitable precursor composition containing a compound of Formula IV

IV

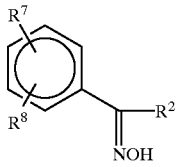

wherein $R^2$ is H; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; $C_2$–$C_4$ alkoxycarbonyl; cyano; or morpholinyl;

$R^7$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2(C_1$–$C_6$ alkyl); $NH(C_1$–$C_6$ alkyl); $N(C_1$–$C_6$ alkyl$)_2$; —$C(R^{11})$=$NOR^{12}$; cyano; nitro; $SiR^{13}R^{14}R^{15}$; $GeR^{13}R^{14}R^{15}$; or $R^7$ is phenyl, benzyl, benzoyl, phenoxy, pyridinyl, pyridinyloxy, thienyl, thienyloxy, furanyl, pyrimidinyl, or pyrimidinyloxy each optionally substituted with one of $R^9$, $R^{10}$, or both $R^9$ and $R^{10}$;

$R^8$ is H; halogen; $C_1$–$C_4$ alkyl; $C_1$–$C_4$ haloalkyl; $C_1$–$C_4$ alkoxy; nitro; or cyano;

$R^9$ and $R^{10}$ are each independently halogen; $C_1$–$C_4$ alkyl; $C_1$–$C_4$ haloalkyl; $C_1$–$C_4$ alkoxy; $C_1$–$C_4$ haloalkoxy; nitro; or cyano;

$R^{11}$ and $R^{12}$ are each independently H; $C_1$–$C_3$ alkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano; and $R^{13}$, $R^{14}$, and $R^{15}$ are each independently $C_1$–$C_6$ alkyl; $C_1$–$C_6$ alkenyl; $C_1$–$C_4$ alkoxy; or phenyl.

The process comprises (a) reacting a compound of Formula V

V

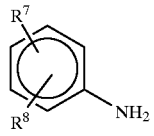

(wherein $R^7$ and $R^8$ are as defined above) with a nitrosating agent to provide a diazonium ion of Formula V*a*

Va

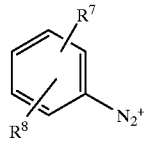

(b) reacting the diazonium ion of Formula V*a* with a compound of Formula VI

VI

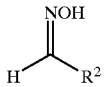

(wherein $R^2$ is defined above) in the presence of a copper salt catalyst to obtain a reaction product containing the compound of Formula IV and greater than 100 ppm copper based on the weight of the Formula IV compound; and (c) separating copper from the Formula IV compound to obtain a purified product composition containing the compound of Formula IV and less than 10 ppm copper based on the weight of the Formula IV compound.

The above process for preparing agriculturally suitable precursor composition can be used as a component of a method for preparing a cyclic urea fungicide, in particular, a cyclic urea fungicide of Formula I

I

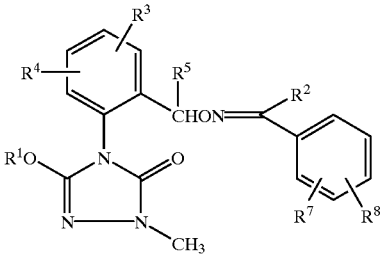

wherein $R^1$ is $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; or $C_3$–$C_6$ cycloalkyl.

$R^3$ and $R^4$ are each independently H; halogen; cyano; nitro; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_1$–$C_6$ alkoxy; $C_1$–$C_6$ haloalkoxy; $C_2$–$C_6$ alkenyloxy; $C_2$–$C_4$ alkoxycarbonyl; or $C_2$–$C_6$ alkynyloxy;

$R^5$ is H; or $C_1$–$C_3$ alkyl; and $R^2$, $R^7$ and $R^8$ are as defined above.

The method comprises (1) preparing an agriculturally suitable precursor composition in accordance with the above process; (2) reacting the oxime of Formula IV from said precursor composition with a compound of Formula III

III

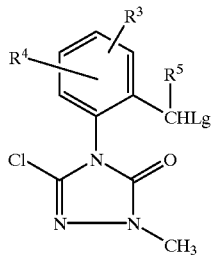

wherein

Lg is halogen; acetoxy; $OSO_2Q$ or $OP(OR^{16})_2$;

Q is $C_1$–$C_6$ alkyl; $C_1$–$C_6$ haloalkyl; or phenyl optionally substituted with $C_1$–$C_3$ alkyl;

$R^{16}$ is $C_1$–$C_6$ alkyl; $C_1$–$C_6$ alkenyl; or phenyl; and $R^2$, $R^3$, $R^4$, $R^5$, $R^7$, $R^8$ are as defined above; to provide a compound of Formula II

II

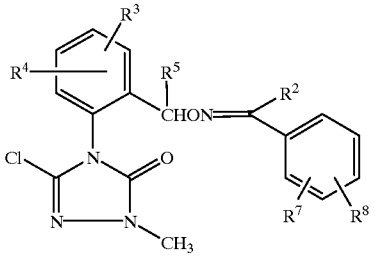

where $R^2$, $R^3$, $R^4$, $R^5$, $R^7$ and $R^8$ are defined as above; and (3) reacting the compound of Formula II with a compound of the Formula $MOR^1$, wherein M is lithium, sodium or potassium and $R_1$ is as defined above, to form the cyclic urea fungicide of Formula I.

DETAILED DESCRIPTION OF THE INVENTION

In the above recitations, the term "alkyl", used either alone or in compound words such as "haloalkyl" denotes straight-chain or branched alkyl; e.g., methyl, ethyl, n-propyl, i-propyl, or the different butyl, pentyl or hexyl isomers. "Alkenyl" denotes straight-chain or branched alkenes; e.g., 1-propenyl, 2-propenyl, and the different butenyl, pentenyl and hexenyl isomers. "Alkenyl" also denotes polyenes such as 1,3-hexadiene. "Alkynyl" denotes straight-chain or branched alkynes; e.g., ethynyl, 1-propynyl, 3-propynyl and the different butynyl, pentynyl and hexynyl isomers. "Alkynyl" can also denote moieties comprised of multiple triple bonds; e.g., 2,4-hexadiyne. "Alkoxy" denotes, for example, methoxy, ethoxy, n-propyloxy, isopropyloxy and the different butoxy, pentoxy and hexyloxy isomers. "Alkenyloxy" denotes straight-chain or branched alkenyloxy moieties. Examples of alkenyloxy include $H_2C{=}CHCH_2O$, $(CH_3)_2C{=}CHCH_2O$, $(CH_3)CH{=}CHCH_2O$, $(CH_3)CH{=}C(CH_3)CH_2O$ and $CH_2{=}CHCH_2CH_2O$. "Alkynyloxy" denotes straight-chain or branched alkynyloxy moieties. Examples include $HC{\equiv}CCH_2O$, $CH_3C{\equiv}CCH_2O$ and $CH_3C{\equiv}CCH_2CH_2O$. The term "halogen", either alone or in compound words such as "haloalkyl", denotes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The term "cycloalkyl" denotes cyclopropyl, cyclobutyl, cyclopentyl and cyclohexyl moieties. The term "nonaromatic heterocyclic ring system" includes fully saturated heterocycles and partially aromatic heterocycles. The total number of carbon atoms in a substituent group is indicated by the "$C_i$–$C_j$" prefix where i and j are numbers from 1 to 6. For example, $C_1$–$C_3$ alkyl designates methyl through propyl; $C_2$ alkoxy designates $CH_3CH_2O$; $C_3$ alkoxy designates, for example, $CH_3CH_2CH_2O$ or $(CH_3)_2CHO$; and $C_2$ alkoxycarbonyl designates $CH_3O(O)C$.

The nitrosating agent used in (a) can be a combination of a strong acid (e.g., HB where B is a weak base) and an organic or inorganic salt (e.g., $JNO_2$ where J is an alkali metal or $C_1$–$C_5$ alkyl group). Alternatively, the nitrosating agent can be a gaseous nitrous oxide (e.g., $N_2O_3$). The reaction of (b) is typically accomplished at a pH that is in the range of from about 2 to 7, preferably in the range of from about 3 to 5. Of note in this invention is the process for preparing agriculturally suitable precursor compositions where the diazonium of Formula V*a* prepared in (a) is used in (b) without isolation.

The purified product composition of Formula IV may be obtained by substantially removing the copper by means of a complexing agent, (e.g. ammonium hydroxide) or by distillation. Preferably, the purified product composition of Formula IV is obtained by steam distillation. Use of a complexing agent or steam distillation for purification typically results in a purified product comprising containing the Formula IV compound together with other by-products. The purified product composition may be further treated to isolate the oxime of Formula IV. However, of note in this invention is the method for preparing cyclic urea fungicides where the purified product composition produced in (c) is used without isolating the oximes of Formula IV.

Reaction steps which may be used in this invention are described further below. These reaction steps may be advantageously combined in a series for preparation of the cyclic urea fungicides.

Step 1

Step 1 forms compounds of Formula IV by diazotizing compounds of Formula V and then reacting the diazonium ion with an oxime of Formula VI in the presence of a copper salt catalyst, then substantially removing the copper by means of a complexing agent or distillation.

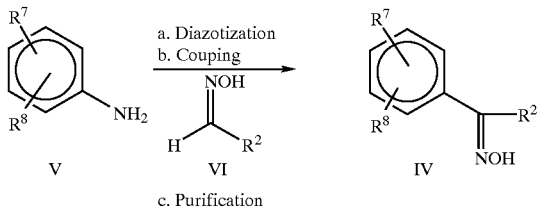

Step 1 (a) - Diazotization

Step 1 (a) can form the diazonium ion of Formula V*a* by reacting compounds of Formula V with an acid of Formula 2 and a nitrite of Formula 3 in a suitable solvent.

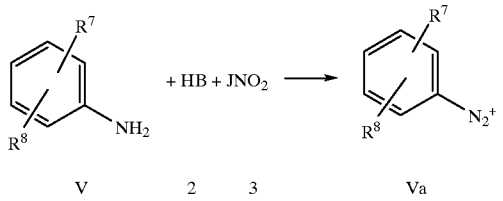

Compounds of Formula V can be obtained commercially from Aldrich or prepared for example, from the reduction of 3-trifluoromethylnitrobenzene as described in *J. Fluorine Chem.,* 281 (1987). Other compounds of Formula V can be prepared by methods of March, J. *Advanced Organic chemistry;* 3rd ed., John Wiley: New York, (1985). Other methods are also known to the skilled artisan. For the process of Step 1 (a), the reaction temperature is typically from −20 to 30 ° C. The temperature is preferably from −5 to 5 ° C. The reaction times are typically from about 0.5 to 2 h. Typically the pressure is about one atmosphere ($1.013\times10^5$ Pa). By suitable solvent for Step 1 (a) is meant, a liquid wherein the reactant(s) can be dissolved and the process of Step 1 proceeds. Suitable solvents include water; ketones such as acetone, acids such as acetic acid or trifluoroacetic acid. The mole ratio of the Formula 2 compound to Formula V compound is typically about 3:1 to 4:1. The mole ratio of the Formula 3 compound to Formula V compound is typically 1:1 to 1.3:1. Strong acids of Formula 2 are useful. Typical acids of Formula 2 are hydrochloric acid, sulfuric acid, borofluoric acid, and trifluoroacetic acid. Nitrites of Formula 3 are useful. Typical nitrites of Formula 3 are sodium nitrite or an organic nitrite such as amylnitrite, and methylnitrite. The product of Formula V*a* can be isolated, by for example filtration, or used directly in the next step without isolation. Formula V*a* compound can also be formed using other processes described in *Aromatic Diazocompounds and Their Technical Application*, Saunders, K. H., (1985).

Step 1 (b) - Coupling

Step 1 (b) forms a compound of Formula IV by reacting a diazonium ion of Formula V*a* with an oxime of Formula VI in a suitable solvent and in the presence of a copper salt catalyst.

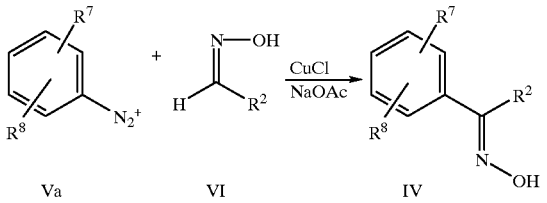

Oxime compounds of Formula VI can be prepared by methods of March, *J. Advanced Organic chemistry;* 3rd ed., John Wiley: New York, (1985) or obtained commercially from Aldrich Chemical Co.. Other methods are also known to the skilled artisan. For the process of Step 1 (b) the reaction temperature is typically from 0 to 60° C. The temperature is preferably from 5 to 25° C., and is more preferably from about 10 to 15° C. The reaction time is typically from about 0.5 to 2 h. Typically the pressure is about one atmosphere. By suitable solvent for Step 1 (b) is meant, a liquid wherein the reactant(s) can be dissolved and the process of Step 1 (b) proceeds. Suitable solvents include water; ketones such as acetone, acids such as acetic acid or trifluoroacetic acid. The mole ratio of the Formula VI compound to Formula V*a* compound is typically about 2:1 to 4:1. Typical copper salt catalysts are copper(I) chloride, copper(II) sulfate, and copper(II) acetate. The amount of the copper is typically from 2 to 10 mol % based on the amount of Formula V compound reacted to form the diazonium ion of Formula V*a*. In the case when copper(I) chloride was used, a small quantity of acetone can also be advantageously employed. In the cases when copper(II) salts are used, a small quantity (e.g., 2 to 5 mol %) of sodium sulfite can be employed. The typical process involves adding a solution of Formula V*a* from Step 1 (a) to a mixture of Formula VI and copper salt buffered by sodium acetate solution in a suitable solvent.

Preferably, the reaction conditions (e.g., temperature, mole ratio, reaction time and solvent) are balanced to achieve a yield from Step 1 (a) and Step 1 (b) (based on Formula V compound reacted to give Formula IV compound) of at least about 75%, more preferably at least 95% before further purification.

Step 1a and Step 1b may be accomplished as separate processes such that the product of Step 1a (i.e., a compound of the diazonium ion of Formula V*a*) is isolated. However, the processes of Step 1a and Step 1b may be combined such that the product of Step 1 a is not isolated but is reacted with an oxime of Formula VI without isolation (e.g., in the same vessel) to give a reaction product containing a compound of Formula IV and greater than 100 ppm copper based on the weight of the Formula IV compound.

The product of Formula IV can be purified, by for example washing with ammonium hydroxide solution, or a steam distillation.

Step 1 (c) - Purification

Typical procedures to obtain Formula IV compounds in usable forms involve either an ammonium hydroxide wash process or a steam distillation.

To form a copper complex, the crude reaction mixture in Step 1 (c) may be extracted into an organic solvent, preferably toluene. The organic phase may then be washed several times with small portions of 15% ammonium hydroxide solution. From 4 to 6 washings are normally sufficient to reduce the amount of copper from greater than 100 ppm to less than 10 ppm (based on the amount of Formula IV compound). Removal of the organic solvent following copper reduction (e.g., by distillation), typically provides a purified product composition which is a viscous oil having a compound IV purity in the range of 50 to 65% by weight. Such viscous oil can be used directly in Step 2.

The crude reaction mixture can also be purified by a steam distillation. Formula IV compounds can be separated from the aqueous distillate either by a filtration or by an extraction with an organic solvent such as toluene. The purified product composition obtained from the steam distillation typically has a compound IV purity of about 90 to 95%.

Step, 2

Step 2 forms compounds of Formula II by reacting compounds of Formula III in a suitable solvent with an oxime of the Formula IV in the presence of a base, or with a preformed salt of said oxime.

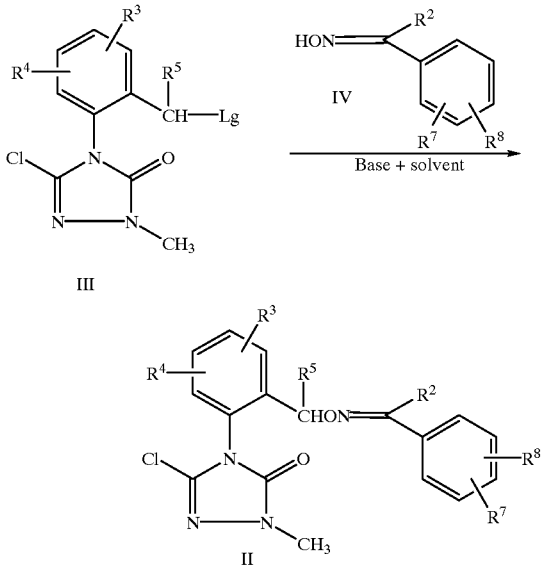

In accordance with this invention, when the oxime starting material in Step 2 is prepared using the Step 1 process described above, the oxime is substantially free of copper which might otherwise substantially inhibit the effect of the base or contaminate the compounds of Formula I or II.

For the process of Step 2, the reaction temperature is typically from about 0 to 200° C. The temperature is preferably from about 0 to 100 ° C. and is more preferably from about 20 to 100° C. Typically, the pressure is from about 1 to 5 atmospheres. By suitable solvent for Step 2 is meant a liquid wherein the reactant(s) can be dissolved and the process of Step 2 proceeds. Suitable solvents for Step 2 include polar aprotic solvents such as acetonitrile, dimethylformamide or dimethylsulfoxide; ethers such as tetrahydrofuran, 1,2-dimethoxyethane, diethoxymethane, or dioxane (e.g. 1,4-dioxane), or diethyl ether; ketones such as acetone or 2-butanone; or acetates such as ethyl acetate; hydrocarbons such as toluene or xylene; or halocarbons such as dichloromethane or chloroform or protic solvents such as methanol, ethanol and water. Suitable bases include alkali metal alkoxides such as potassium tert-butoxide, inorganic bases such as sodium hydride, sodium hydroxide, potassium hydroxide, sodium carbonate, and potassium carbonate, or tertiary amines such as triethylamine, pyridine, 1,8-diazabicyclo-[5.4.0]undec-7-ene (DBU), or triethylenediamine. The reaction times are typically from about 0.5 to 48 h. The mole ratio of the cyclic urea of Formula III to the oxime is typically from about 1:1 to 1:3 and the mole ratio of the oxime to the base is typically from about 1:0.75 to 1:10 (e.g. 1:1 to 1:10).

Preferred Step 2 processes include those wherein the reaction time is from about 1 to 6 h (e.g., 2 to 6 h); the temperature is from about 0 to 100° C.; the pressure is about 1 atmosphere; the mole ratio of cyclic urea to oxime is from about 1:1 to 1:2; the mole ratio of the oxime to base is from about 1:0.75 to 1:5 (e.g. 1:1 to 1:5); the solvent is tetrahydrofuran, dimethylformamide, diethoxymethane, 1,2-dimethoxyethane, acetonitrile, dimethylsulfoxide, dioxane (e.g., 1,4-dioxane), methanol, toluene, water, or a mixture thereof (optionally in the presence of a phase transfer catalyst), and the base is sodium hydride, sodium hydroxide, potassium hydroxide, sodium carbonate, potassium carbonate, or potassium t-butoxide. Particularly preferred for achieving high yields of Formula II compounds are processes of Step 2 wherein the reaction time is from about 2 to 6 h; the temperature is from about 20 to 100° C.; the pressure is about 1 atmosphere; the mole ratio of cyclic urea to oxime is about 1:1; the mole ratio of the oxime to base is about 1:0.75 to 1:5 (e.g., 1:1 or, more preferably, 1:0.75); the solvent is tetrahydrofuran or 1,4-dioxane; and the base is sodium hydroxide, potassium hydroxide or sodium hydride. Alternatively, compounds of Formula III can be reacted with a preformed salt of the oxime. When hydroxides are used as base, water is formed as a by-product. This water by-product can be left in the reaction mixture or partially or totally removed by distillation or other means during the course of the reaction. Compounds of Formula II can be isolated by standard methods such as removal of most solvent under reduced pressure, addition of water and filtration. Alternatively for product isolation, the reaction mixture can be poured into a methylene chloride/hexane mixture, filtered through silica gel and volatiles removed.

Preferred oximes of Formula IV for use in this process include 1-[3-(trifluoromethyl)phenyl]ethanone oxime, 1-[3,5-(bistrifluoromethyl)phenyl]ethanone oxime, and 1-[3,5-dichlorophenyl]ethanone oxime. Examples of the process of Step 2 include the reaction of 5-chloro-4-[2-(chloromethyl)phenyl]-2,4-dihydro-2-methyl-3H-1,2,4-triazol-3-one one with -1-[3,5-(bistrifluoromethyl)phenyl]ethanone oxime to form 5-chloro-2,4-dihydro-2-methyl-4-[2-[[[[1-[3(trifluoromethyl)phenyl]-ethylidene]amino]oxy]methyl]phenyl]-3H-1,2,4-triazol-3-one; the reaction of 5-chloro-4-[2-(chloromethyl)phenyl]-2,4-dihydro-2-methyl-3H-1,2,4-triazol-3-one with 1-[3,5-(bistrifluoromethyl)phenyl]ethanone oxime to form 5-chloro-2,4-dihydro-2-methyl-4-[2-[[[[1-[3(bistrifluoromethyl)phenyl]-ethylidene]amino]oxy]methyl]phenyl]-3H- 1,2,4-triazol-3-one.

Compounds where Lg is Cl or Br are preferred for this process, with Cl being most preferred. Preferably, the reaction conditions (e.g., temperature, mole ratio, reaction time, base and solvent) are balanced to achieve a Step 2 yield (based on a Formula III compound reacted to give a Formula II compound) of at least about 75%, more preferably at least about 85%.

The product of process Step 2 may be further reacted with a compound of $MOR^1$ in a suitable solvent. This is illustrated in the process of Step 3.

Step 3

Step 3 forms compounds of Formula I by reacting compounds of Formula II with an alkoxylating agent of the formula $MOR^1$ in a suitable solvent.

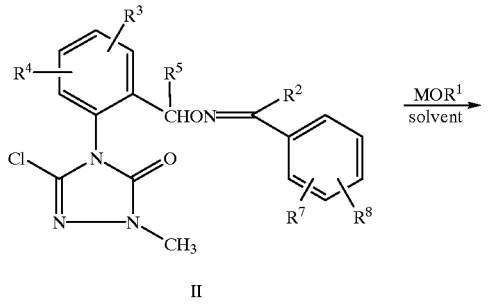

-continued

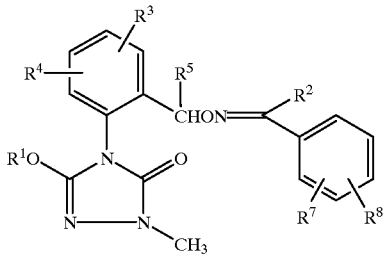

I

Alkoxylating compounds of the formula $MOR^1$ are defined above. For the process of Step 3, the reaction temperature is typically from about 0 to 200° C. The temperature is preferably from about 0 to 100° C. Typically the pressure is from about 1 to about 5 atmospheres. By suitable solvent for Step 3 is meant, a liquid wherein the reactant(s) can be dissolved and the process of Step 3 proceeds. Suitable solvents for Step 4 include ethers such as tetrahydrofuran, dimethoxyethane, diethoxymethane, diethyl ether, dimethyl acetamide or 1,4-dioxane, and alcohols such as methanol, and ethanol. Typically when an alcohol is used as a solvent, methanol would be used with $MOCH_3$, ethanol would be used for $MOCH_2CH_3$. The reaction times are typically from about 0.5 to 48 h. The mole ratio of the coupled product of Formula II to alkoxylating agent is typically from about 1:1 to 1:20. Preferred Step 3 processes include those wherein the reaction time is from about 1 to 6 h (e.g., 2 to 6 h); the temperature is from about 0 to 100° C.; the pressure is about 1 atmosphere; the mole ratio of coupled product to alkoxylating agent is from about 1:1 to 1:5; the solvent is tetrahydrofuran, methanol, diethoxymethane, dimethyl acetamide or 1,4-dioxane; and the alkoxylating agent is sodium methoxide or potassium methoxide. Particularly preferred for achieving high yields of Formula I compounds are processes of Step 3 wherein the reaction time of Step 3 is from about 1 to 6 h (e.g., 2 to 6 h); the temperature is from about 0 to 100° C.; the pressure is about 1 atmosphere; the mole ratio of coupled product to alkoxylating agent is about 1:2, the solvent is tetrahydrofuran, dimethyl acetamide or 1,4-dioxane; and the alkoxylating agent is sodium methoxide. The methoxide can be preformed or formed in situ, by for example reaction of sodium hydride or sodium hydroxide with methanol.

Preferred alkoxylating agents of Formula $MOR^1$ for use in this process include sodium methoxide and potassium methoxide. Examples of the process of Step 3 include the reaction of sodium methoxide with 5-chloro-2, 4-dihydro-2-methyl-4-[2-[[[[1-[3(trifluoromethyl)phenyl]-ethylidene]amino]oxy]methyl]phenyl]-3H-1,2,4-triazol-3-one to form 2,4-dihydro-5-methoxy-2-methyl-4-[2-[[[[1-[3-trifluoromethyl)phenyl]-ethylidene]amino]oxy]methyl]phenyl]- 3H-1,2,4-triazol-3-one; the reaction of potassium methoxide with 5-chloro-2, 4-dihydro-2-methyl-4-[2-[[[[1-[3(trifluoromethyl)phenyl]-ethylidene]amino]oxy]methyl]phenyl]- 3H-1,2,4-triazol-3-one to form 2,4-dihydro-5-methoxy-2-methyl-4-[2-[[[[1-[3-trifluoromethyl)phenyl]-ethylidene]amino]oxy]methyl]phenyl]-3H-1,2,4-triazol-3-one.

Preferably, the reaction conditions (e.g., temperature, mole ratio, reaction time, base and solvent) are balanced to achieve a Step 3 yield (based on a Formula II compound reacted to give a Formula I compound) of at least about 75%, more preferably at least about 85%.

Step 2 and Step 3 may be accomplished as separate processes such that the product of Step 2 (i.e., the compound of Formula II) is isolated. However, the processes of Step 2 and Step 3 may be combined such that the product of Step 2 is not isolated but is reacted with an alkoxylating agent without isolation (e.g., in the same vessel) to give a product of Formula I. It is noteworthy that Steps 2 and 3 can typically be carried out sequentially in the same vessel without isolation of compounds of Formula II by adding alkoxylating agent (e.g., methoxide) to the product of Step 2 in situ, as described in Example 5.

Preferably, the reaction conditions (e.g., temperature, mole ratio, reaction time, base and solvent) are balanced to achieve a combined Step 2 and 3 yield (based on a Formula III compound reacted to give a Formula I compound) of at least about 60%, more preferably at least about 70%.

Examples of the combined processes of Steps 2 and 3 include the reaction of 5-chloro-2, 4-dihydro-2-methyl-4-[2-[[[[1-[3(trifluoromethyl)phenyl]-ethylidene]amino]oxy]methyl]phenyl]- 3H-1,2,4-triazol-3-one with 1-[3-(trifluoromethyl)phenyl]ethanone oxime in the presence of a base (e.g., KOH, NaH or K t-butoxide) in a suitable solvent (e.g., THF) and the subsequent reaction of the product of that reaction with methanol in the THF solution to form 2,4-dihydro-5-methoxy-2-methyl-4-[2-[[[[1-[3-(trifluoromethyl)phenyl]-ethylidene]amino]oxy]methyl]phenyl]- 3H-1,2,4-triazol-3-one; the reaction of 5-chloro-2, 4-dihydro-2-methyl-4-[2-[[[[1-[3(trifluoromethyl)phenyl]-ethylidene]amino]oxy]methyl]phenyl]- 3H-1,2,4-triazol-3-one with 1-[3,5-(bistrifluoromethyl)phenyl]ethanone oxime in the presence of a base and the subsequent reaction of the product of that reaction with methanol to form 5-chloro-2, 4-dihydro-2-methyl-4-[2-[[[[1-[3(trifluoromethyl)phenyl]-ethylidene]amino]oxy]methyl]phenyl]-3H-1,2,4-triazol-3-one.

The compounds of Formula II can be provided from the compounds of Formula III in accordance with Step 2; the compounds of Formula III can be provided in accordance with U.S. patent application Ser. No. 60/007838 and PCT International Application No. PCT/US96/19207; and the compounds of Formula IV can be provided from the compounds of Formula V in accordance with Step 1. Accordingly, Step 2 can be combined with Step 1 to readily provide cyclic urea fungicides of Formula II which can in turn be readily reacted to provide cyclic urea fungicides of Formula I. For example, this invention provides a process for the preparation of cyclic urea fungicides of Formula I comprising reacting an aniline of Formula V with a diazonium ion of Formula V*a,* and reacting the diazonium ion with a compound of Formula VI in the presence of a copper salt catalyst to give an oxime of Formula IV, which is then coupled with a cyclic urea of Formula III in the presence of a suitable base which has sufficient basicity to form an oxime salt, or with the preformed salt of an oxime of Formula IV and in a suitable solvent at a temperature of from about 0 to 200° C. and a pressure of from about 1 to 5 atmospheres to give a compound of Formula II, and then treating a compound of Formula II with an excess of alkoxylating agent in a suitable solvent at a temperature of about 0 to 200° C. and a pressure of from about 1 to 5 atmospheres to give cyclic urea fungicides of Formula I. Thus, preferably, the reaction conditions (e.g. temperature, mole ratio, reaction time and solvent) are balanced to achieve a combined Step 1, 2, 3 and 4 yield (based on a Formula V compound reacted to give a Formula I compound) of at least about 50%, more preferably at least about 60%. Thus, for example 2,4-dihydro-5-methoxy-2-methyl-4-[2-[[[[1-[3-trifluoromethyl)phenyl]-ethylidene]amino]oxy]methyl]phenyl]- 3H-1,2,4-triazol-3-one can be advantageously prepared by treating 3-(trifluoromethyl) aniline with sodium nitrite and sulfuric acid in an aqueous slurry, the resulting diazonium ion can be reacted with acetaldoxime in the presence of copper acetate, and the desired product (i.e., 1-[3-(trifluoromethyl)phenyl]ethanone oxime) can be reacted (after separation of copper using ammonium hydroxide wash) with 5-chloro-4- [2-(chloromethyl)phenyl]-2,4-dihydro-2-methyl-3H- 1,2,4-triazol-3-one in the presence of a base selected from the group consisting of sodium hydride, sodium hydroxide, potassium hydroxide, sodium carbonate, potassium carbonate, and potassium t-butoxide (where the mole ratio of the oxime to base is from about 1:0.75 to 1:5 (e.g., 1:1 to 1:5) and the mole ratio of the cyclic urea to oxime is from about 1:1 to 1:2) in a solvent selected from the group consisting of tetrahydrofuran, dimethylformamide, diethyoxymethane, 1,2-dimethoxyethane, acetonitrile, dimethylsulfoxide, dioxane (e.g., 1,4-dioxane), methanol, toluene, water and mixtures thereof (optionally in the presence of a phase transfer catalyst) at a temperature of from about 0 to 100° C. for from about 1 to 6 h (e.g., 2 to 6 h); and the desired product 5-chloro-2, 4-dihydro-2-methyl-4-[2-[[[[1-[3(trifluoromethyl)phenyl]-ethylidene]amino]oxy]methyl]phenyl]- 3H-1,2,4-triazol-3-one can be reacted (with or without isolation) with sodium methoxide or potassium methoxide in a mole ratio of from about 1:1 to 1:5 at a temperature of from about 0 to 100° C. in a solvent selected from the group consisting of tetrahydrofuran, methanol, diethoxymethane, and 1,4-dioxane for from about 1 to 6 h (e.g. 2 to 6 h) to obtain said 2,4-dihydro-5-methoxy-2-methyl-4-[2-[[[[1-[3-trifluoromethyl)phenyl]-ethylidene]amino]oxy]methyl]phenyl]- 3H-1,2,4-triazol-3-one.

Preferred processes for reasons of cost, ease of synthesis, and fungicidal activity are processes for preparing compounds of Formula I wherein $R^1$ is $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl or $C_3$–$C_6$ cycloalkyl; $R^2$ is $C_1$–$C_6$ alkyl; $R^5$ is H or $C_1$–$C_3$ alkyl; $R^7$ is H, 1–2 halogen, $C_1$–$C_6$ alkyl, $C_1$–$C_6$ haloalkyl, $C_1$–$C_6$ alkoxy or $C_1$–$C_6$ haloalkoxy; $R^8$ is H, halogen, $C_1$–$C_4$ alkyl, $C_1$–$C_4$ haloalkyl or $C_1$–$C_4$ alkoxy; $R^{13}$, $R^{14}$, and $R^{15}$ are each independently $C_1$–$C_6$ alkyl, $C_1$–$C_6$ alkenyl, $C_1$–$C_4$ alkoxy or phenyl; and $R^3$, and $R^4$ are each independently H, $CH_3$, $OCH_3$, Br or Cl. Particularly preferred are processes for preparing compounds of Formula I wherein $R^2$ is $CH_3$; $R^5$ is H; $R^7$ is 1–2 halogen or $CF_3$; $R^8$ is H or $CF_3$ and $R^1$ is $CH_3$.

The following examples are representative of the production of cyclic urea fungicides. $H^1$NMR Spectra are reported in ppm downfield from tetramethylsilane; s=singlet, d=doublet, m=multiplet.

EXAMPLE 1

Preparation of 1-[3-(trifluoromethyl)phenyl] ethanone oxime (Step 1)

To a three-neck indented, Morton style flask equipped with a sidearm for thermometer charged with 80 mL (240 mmol) of 3N sulfuric acid was added 10 mL (80 mmol) of 3-(trifluoromethyl)aniline (Aldrich Chemical Co.). The resulting suspension turned into a clear solution upon heating to 65° C. The solution was stirred vigorously and cooled to −5° C. using an acetone/ice bath to give a slurry. To the slurry was added a solution of 5.85 g (84.8 mmol) of sodium nitrite in 25 mL of water. The rate of addition was carefully adjusted so the internal reaction temperature was maintained between −5 and 0° C. The mixture was stirred at that temperature for 30 min. The diazonium thus obtained appears as a thin slurry. The slurry thickened when a solution of 20 g (244 mmol) of sodium acetate in 50 mL of water was added. Meanwhile, in another flask, 19 mL (320 mmol) of acetaldoxime, 1.50 g (8 mmol) of copper (II) acetate, 0.5 g (4 mmol) of sodium sulfite, and 20 g (244 mmol) of sodium acetate were combined and cooled to about 10° C. To this solution was added via a cannula or additional funnel the diazonium mixture. Immediate gas ($N_2$) evolution was observed, and a two phase mixture (dark green oil and aqueous) was obtained. The mixture was stirred for 30 min before the reaction was worked up. To the mixture was added about 300 mL of toluene and the organic phase separated from the aqueous. The aqueous phase was extracted with another 100 mL of toluene. The combined toluene extracts (greenish color) were washed with 15% ammonium hydroxide solution (5×20 mL). Analysis using copper test strips from EM Science indicated the copper (I/II) content to be less than 10 ppm as compared to greater than 100 ppm before the ammonium hydroxide wash. The organic phase (orange color) was washed with 20 mL of brine and dried over magnesium sulfate. Removal of volatiles on the rotovap gave an orange oil which turned into a semi-solid upon fuirther drying on the vacuum pump to give 13.7 g (84%) of a solid product. In the analytical assay, it was found to contain 58.9% of the desired oxime product.

EXAMPLE 2

Preparation of 1-[3-(trifluoromethyl)phenyl]ethanone oxime (Step 1) To a three-neck indented, Morton style flask equipped with a sidearm for thermometer charged with 320 mL (1080 mmol) of 4N sulfuric acid was added 40 mL (320 mmol) of 3-(trifluoromethyl)aniline. The solution was cooled to -5° C. using an acetone/ice bath to give a slurry. To the slurry was added a solution of 28.0 (406 mmol) of sodium nitrite in 80 mL of water. The rate of addition was carefully adjusted so the internal reaction temperature was maintained between −5 and 0° C. The mixture was stirred at that temperature for 30 min. The diazonium thus obtained appears as a thin slurry. The slurry thickened when a solution of 15 g (183 mmol) of sodium acetate in 100 mL of water was added. Meanwhile, in another flask, 80 mL (1350 mmol) of acetaldoxime (AAO), 6.0 g (32 mmol) of copper (II) acetate, 2.0 g (16 mmol) of sodium sulfite, and 240 g (2900 mmol) of sodium acetate were combined and cooled to about 10° C. To this solution was added via a cannula or additional funnel the diazonium mixture. Immediate gas ($N_2$) evolution was observed, and a two phase mixture (dark green oil and aqueous) was obtained. The mixture was stirred for 30 min at room temperature. The oil on the bottom was separated from the aqueous phase and transferred to another flask. 11.0 g (320 mmol) of hydroxylamine and 22.0 g (320 mmol) of potassium carbonate was added together with 200 ml of water. The mixture was subjected to a steam distillation. Over a period of 2 h, a total of 1700 mL of distillate was obtained. The product first existed as a slightly yellow oil depositing on the bottom of the collecting flask. Upon chilling, product solidified. A total of 35.9 g of the desired product was obtained after filtration with an assay purity of 89.7%.

EXAMPLE 3

Preparation of 5-chloro-2, 4-dihydro-2-methyl-4-[2-[[[[1-[3(trifluoromethyl)phenyl]-ethylidene]amino]oxy]methyl]phenyl]-3H-1,2,4-triazol-3-one (Step 2)

A 100 mL 2-necked round bottom flask is fitted with thermometer, reflux condenser capped with nitrogen bypass and magnetic stirrer. The flask is charged with 30 mL tetrahydrofuran and 0.22 g 60% sodium hydride in mineral oil (5.5 mmol). To this is added with stirring, 1.02 g 1-[3-(trifluoromethyl)phenyl]ethanone oxime (5 mmol) resulting in a vigorous reaction with off-gassing. When the off-gassing ceases (approximately two minutes), 1.29 g of 5-chloro-4-[2-(chloromethyl)phenyl]-2,4-dihydro-2-methyl-3H-1,2,4-triazol-3-one (5 mmol) is added. The resultant mixture is heated at reflux (approximately 62° C.) for 3 h. The mixture is allowed to cool to room temperature and poured into approximately 100 mL of 30% methylene chloride in hexane. This mixture is filtered through a 1 inch thick bed of silica gel which is then rinsed with approximately 500 mL 40% ethyl acetate in methylene chloride. The organic filtrates are combined and volatiles are removed on the rotary flash evaporator to yield 2.13 g of yellow oil. Addition of hexane to the oil results in the formation of crystals which are then triturated with hexane. Filtration and drying gives 1.83 g of solid product, m.p. 95–97° C. $H^1$NMR ($CDCl_3$): δ2.20 (s,3H), 3.47 (s,3H), 5.19 (d,1H), 5.31 (d,1H), 7.26 (m,1H), 7.54 (m,5H), 7.83 (m,2H).

EXAMPLE 4

Preparation of 2,4-dihydro-5-methoxy-2-methyl-4-[2-[[[[1-[3-trifluoromethyl)phenyl]-ethylidene]amino]oxy]methyl]phenyl]- 3H-1,2,4-triazol-3-one (Step 3)

A 100 mL 1-necked round bottom flask is fitted with a magnetic stirrer and reflux condenser capped with a nitrogen bypass. The flask is charged with 50 mL of tetrahydrofuran, 2.12 g of 5-chloro-2,4-dihydro-2-methyl-4-[2-[[[[1-[3-(trifluoromethyl)phenyl]-ethylidene]amino]oxy]methyl]phenyl]-3H-1,2,4-triazol-3-one (5 mmol) and 1.19 g of 25% sodium methoxide in methanol (5.5 mmol). The mixture is heated to reflux with stirring. After 4 h, 0.10 g of 25% sodium methoxide in methanol is added. After an additional 2 h, 0.30 g of 25% sodium methoxide in methanol is added. The mixture is then stirred at reflux for one additional hour at which time analysis of an aliquot by high pressure liquid chromatography indicates the presence of essentially no starting material. The mixture is allowed to cool to room temperature and left stirring overnight. The mixture is then worked up as in Example 3 to yield 2.06 g of pale yellow oil which crystallized upon seeding with an authentic sample of 2,4-dihydro-5-methoxy-2-methyl-4-[2[[[[1-[3-(trifluoromethyl)phenyl-ethylidene]amino]oxy]methyl]phenyl]-3H-1,2,4-triazol-3-one. Trituration with hexanes followed by filtration and drying gave 1.97 g of white solid, m.p. 97–98.5° C. A portion (1.00 g) of this was recrystallized from 10 mL of 10% ethyl acetate-hexane to yield 0.94 g of white solid, m.p. 101–102° C. $H^1$NMR ($CDCl_3$) δ 2.21 (s,3H), 3.40 (s,3H), 3.89 (s,3H), 5.24 (d,2H), 5.28 (d,2H), 7.26 (m,1H), 7.47 (m,3H), 7.58 (m,2H), 7.85 (m,2H).

EXAMPLE 5

Preparation of 2,4-dihydro-5-methoxy-2-methyl-4-2-[[[[1-[3-(trifluoromethyl)phenyl]-ethylidene]amino]oxy]methyl]phenyl]- 3H-1,2,4-triazol-3-one (Steps 2 and 3)

A 200 mL 2-necked round bottom flask is fitted with thermometer, reflux condenser capped with nitrogen bypass and magnetic stirrer. The flask is charged with 100 mL of tetrahydrofuran, 1.28 g of 60% sodium hydride in mineral oil (32 mmol). To this is added with stirring 2.03 g of 1-[3-(trifluoromethyl)phenyl]ethanone oxime (10 mmol). When offgassing ceases (approximately 15 min) 2.58 g of 5-chloro-4-[2-(chloromethyl)phenyl]-2,4-dihydro-2-methyl-3H-1,2,4-triazol-3-one heterocycle (10 mmol) is added. The resultant mixtures is heated to reflux approximately 65° C. for 5 h. It is then allowed to cool to approximately 60° C. and 2.56 g of methanol (80 mmol) is added slowly. The resultant mixture is heated to reflux (approximately 65° C.) for an additional 3 h at which time analysis of an aliquot by high pressure liquid chromatography shows the reaction to be essentially complete. The mixture is allowed to cool to room temperature and worked up as described in Examples 3 and 4 giving 4.15 g of red oil. Addition of hexane results in crystallization of the oil. Trituration of these crystals with hexane followed by filtration and drying gives 3.32 g of yellow solid m.p. 96–99° C.

EXAMPLE 6

Preparation of 5-chloro-2,4-dihydro-2-methyl-4-[2-[[[[1-[3(trifluoromethyl)phenyl]-ethylidene]amino]oxy]methyl]phenyl]-3H-1,2,4-triazol-3-one (Step 2)

A 100 mL 2-necked round bottom flask is fitted with thermometer, distillation head with nitrogen-bypass, and magnetic stirrer. The flask is charged with 25 mL of tetrahydrofuran, 0.18 g of potassium hydroxide (85% assay, 2.75 mmol), 0.51 g of 1-[3-(trifluoromethyl)phenyl]ethanone oxime (2.5 mmol) and 0.65 g of 5-chloro-4-[2-(chloromethyl)phenyl]-2,4-dihydro-2-methyl-3H-1,2,4-triazol-3-one (2.5 mmol). The resultant mixture is heated and reaction followed by high pressure liquid chromatography (HPLC). After 0.5 h at 50° C., 10 mL of tetrahydrofuran is added. After 1 h at 65° C., 10 mL of distillate is removed from the reaction. The mixture is heated at 66° C. for an additional 2 h, at which analysis of a reaction aliquot by HPLC indicated the absence of starting material oxime. The mixture is allowed to cool to room temperature. It is worked up using the method in Example 3 by addition to methylene chloride in hexanes followed by silica gel filtration and solvent removed to yield 1.02 g of yellow crude product. Quantitative analysis by HPLC indicated this to be 89% desired product 5-chloro-2, 4-dihydro-2-methyl-4-[2-[[[[1-[3(trifluoromethyl)phenyl]-ethylidene]amino]oxy]methyl]-phenyl]- 3H-1,2,4-triazol-3-one.

EXAMPLE 7

Preparation of 2,4-dihydro-5-methoxy-2-methyl-4-[2-[[[[1-3-(trifluoromethyl)phenyl]-ethylidene]amino]oxy]methyl]phenyl]-3H-1,2,4-triazol-3-one (Steps 2 and 3)

A 200 mL 2-necked round bottom flask is fitted with thermometer, distillation head with nitrogen-bypass, and magnetic stirrer. The flask is charged with 100 mL of tetrahydrofuran, 0.52 g of potassium hydroxide (85% assay, 7.9 mmol), 1.09 g of 1-[3-(trifluoromethyl)phenyl]ethanone oxime (7.2 mmol) and 1.93 g of 5-chloro-4-[2-(chloromethyl)phenyl]-2,4-dihydro-2-methyl-3H-1,2,4-triazol-3-one (96% pure, 7.2 mmol). The resultant mixture is stirred at room temperature (approximately 23° C.) and reaction is followed by high pressure liquid chromatography (HPLC). After 20 h, the mixture is heated and approximately 40 mL of distillate is removed. The mixture is then heated for one additional hour at approximately 65° C., at which analysis of an aliquot by HPLC shows very little oxime remaining. To the mixture is then added 3.11 g of 25% sodium methoxide in methanol (14.4 mmol) and the resultant mixture is heated at approximately 65° C. for 4.5 h. To the mixture is then added 1.04 g of 25% sodium methoxide in methanol. The mixture is heated for 1.5 h at approximately 65° C. and then allowed to stir overnight at room temperature. The mixture is then heated to approximately 65° C. for 2 h at which analysis of an aliquot by HPLC indicated very little starting materials remaining. The reaction mixture is allowed to cool to room temperature. It is worked up as described in Examples 5 and 6 giving 3.06 g of yellow oil. Quantitative analysis by HPLC indicated this to be 83% desired product 2,4-dihydro-5-methoxy-2-methyl-4-[2-[[[[1-[3-(trifluoromethyl)phenyl]-ethylidene] amino]oxy]methyl]phenyl]- 3H-1,2,4-triazol-3-one.

EXAMPLE 8

Preparation of 2,4-dihydro-5-methoxy-2-methyl-4-[2-[[[[1-[3-trifluoromethyl)phenyl]-ethylidene] amino]oxy]methyl]phenyl]- 3H-1,2,4-triazol-3-one (Steps 2 and 3)

525 g of 9.90% triazol solution (0.201 mol) was distilled until 328 g of 1,4-dioxane was collected. The residue was cooled to about 40° C. and 40.6 g (0.200 mol) of oxime was added. The solution was then reheated to 75° C. and 12.0 g (0.15 mol) of NaOH was added during 30 min. The resulting reaction mass was then stirred for 2 h at 75° C.

After 2 h, the mixture was cooled to 65° C. and 65 g (0.300 mol) of 25% NaOMe was added. Heating at 65° C. was continued for 5 h. The mixture was then cooled to room temperature and 300 mL of water and 250 mL of n-hexane were added along with 1 g of seed crystals. The resulting mixture was stirred in an ice bath for 1.5 h before filtration. The solids were washed with water and hexane and then dried to give 56.3 g. HPLC analysis showed that the product was 89.1% pure, or a yield of 59.7% based on oxime. Recrystallization can be used if higher purity material is desired.

We claim:

1. A process for preparing an agriculturally suitable precursor composition containing a compound of Formula IV

IV

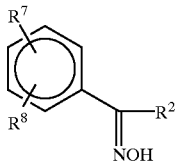

wherein $R^2$ is H; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; $C_2$–$C_4$ alkoxycarbonyl; cyano; or morpholinyl;

$R^7$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2$($C_1$–$C_6$ alkyl); NH($C_1$–$C_6$ alkyl); N($C_1$–$C_6$ alkyl)$_2$; —C($R^{11}$)=NO$R^{12}$; cyano; nitro; Si$R^{13}R^{14}R^{15}$; Ge$R^{13}R^{14}R^{15}$; or $R^7$ is phenyl, benzyl, benzoyl, phenoxy, pyridinyl, pyridinyloxy, thienyl, thienyloxy, furanyl, pyrimidinyl, or pyrimidinyloxy each optionally substituted with one of $R^9$, $R^{10}$, or both $R^9$ and $R^{10}$;

$R^8$ is H; halogen; $C_1$–$C_4$ alkyl; $C_1$–$C_4$ haloalkyl; $C_1$–$C_4$ alkoxy; nitro; or cyano;

$R^9$ and $R^{10}$ are each independently halogen; $C_1$–$C_4$ alkyl; $C_1$–$C_4$ haloalkyl; $C_1$–$C_4$ alkoxy; $C_1$–$C_4$ haloalkoxy; nitro; or cyano;

$R^{11}$ and $R^{12}$ are each independently H; $C_1$–$C_3$ alkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano; and $R^{13}$, $R^{14}$, and $R^{15}$ are each independently $C_1$–$C_6$ alkyl; $C_1$–$C_6$ alkenyl; $C_1$–$C_4$ alkoxy; or phenyl, comprising:

(a) reacting a compound of Formula V

V

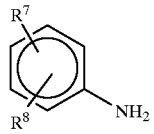

with a nitrosating agent to provide a diazonium ion of Formula V*a*

Va

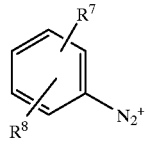

(b) reacting the diazonium ion of Formula V*a* with a compound of Formula VI

VI

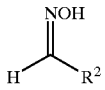

in the presence of a copper salt catalyst to obtain a reaction product containing the compound of Formula IV and greater than 100 ppm copper based on the weight the Formula IV compound; and (c) separating copper from the Formula IV compound to obtain a purified product composition containing the compound of Formula IV and less than 10 ppm copper based on the weight of the Formula IV compound.

2. A method for preparing a cyclic urea fungicide, in particular, a cyclic urea fungicides of Formula I

I

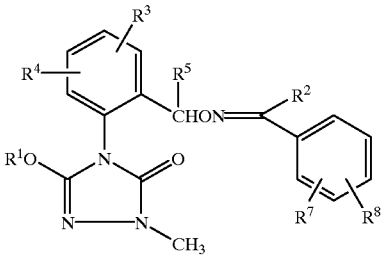

wherein $R^1$ is $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; or $C_3$–$C_6$ cycloalkyl.

$R^2$ is H; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_2$–$C_6$ alkenyl;

$C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; $C_2$–$C_4$ alkoxycarbonyl; cyano; or morpholinyl;

$R^3$ and $R^4$ are each independently H; halogen; cyano; nitro; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_1$–$C_6$ alkoxy; $C_1$–$C_6$ haloalkoxy; $C_2$–$C_6$ alkenyloxy; $C_2$–$C_4$ alkoxycarbonyl; or $C_2$–$C_6$ alkynyloxy;

$R^5$ is H; or $C_1$–$C_3$ alkyl;

$R^7$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2$($C_1$–$C_6$ alkyl); NH($C_1$–$C_6$ alkyl); N($C_1$–$C_6$ alkyl)$_2$; —C($R^{11}$)═NO$R^{12}$; cyano; nitro; Si$R^{13}R^{14}R^{15}$; Ge$R^{13}R^{14}R^{15}$; or $R^7$ is phenyl, benzyl, benzoyl, phenoxy, pyridinyl, pyridinyloxy, thienyl, thienyloxy, furanyl, pyrimidinyl, or pyrimidinyloxy each optionally substituted with one of $R^9$, $R^{10}$, or both $R^9$ and $R^{10}$;

$R^8$ is H; halogen; $C_1$–$C_4$ alkyl; $C_1$–$C_4$ haloalkyl; $C_1$–$C_4$ alkoxy; nitro; or cyano;

$R^9$ and $R^{10}$ are each independently halogen; $C_1$–$C_4$ alkyl; $C_1$–$C_4$ haloalkyl; $C_1$–$C_4$ alkoxy; $C_1$–$C_4$ haloalkoxy; nitro; or cyano;

$R^{11}$ and $R^{12}$ are each independently H; $C_1$–$C_3$ alkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano; and $R^{13}$, $R^{14}$, and $R^{15}$ are each independently $C_1$–$C_6$ alkyl; $C_1$–$C_6$ alkenyl; $C_1$–$C_4$ alkoxy; or phenyl, comprising (1) preparing an agriculturally suitable precursor composition in accordance with claim 1;

(2) reacting the oxime of Formula IV from said precursor composition with a compound of Formula III

III

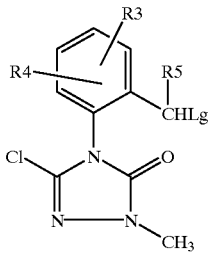

wherein

Lg is halogen; acetoxy; $OSO_2Q$ or $OP(OR^{16})_2$;

Q is $C_1$–$C_6$ alkyl; $C_1$–$C_6$ haloalkyl; or phenyl optionally substituted with $C_1$–$C_3$ alkyl; and $R^{16}$ is $C_1$–$C_6$ alkyl; $C_1$–$C_6$ alkenyl; or phenyl;

to provide a compound of Formula II

II

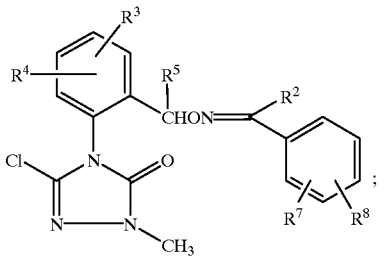

and (3) reacting the compound of Formula II with a compound of the Formula $MOR^1$, wherein M is lithium, sodium or potassium to form the cyclic urea fungicide of Formula I.

* * * * *